United States Patent
Shishido et al.

(10) Patent No.: US 8,475,833 B2
(45) Date of Patent: Jul. 2, 2013

(54) JELLY-FORM PREPARATION AND METHOD FOR PRODUCING JELLY-FORM PREPARATION

(75) Inventors: Takuya Shishido, Ibaraki (JP); Daisuke Asari, Ibaraki (JP); Mitsuhiko Hori, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/546,580

(22) Filed: Jul. 11, 2012

(65) Prior Publication Data

US 2013/0017230 A1    Jan. 17, 2013

(30) Foreign Application Priority Data

Jul. 13, 2011  (JP) ................ 2011-154897

(51) Int. Cl.
*A61K 47/00* (2006.01)
(52) U.S. Cl.
USPC ......................................... 424/439
(58) Field of Classification Search
None
See application file for complete search history.

(56) References Cited

U.S. PATENT DOCUMENTS

| 4,500,453 A | 2/1985 | Shank |
| 5,932,235 A | 8/1999 | Ninomiya et al. |
| 2010/0063110 A1 | 3/2010 | Meyer et al. |
| 2010/0112015 A1 | 5/2010 | Nogami |
| 2010/0278899 A1* | 11/2010 | Sugiura et al. ............... 424/439 |

FOREIGN PATENT DOCUMENTS

| JP | 09-187233 A | 7/1997 |
| JP | 2004-099558 A | 4/2004 |
| JP | 2005-511522 A | 4/2005 |
| JP | 2009-507854 A | 2/2009 |
| WO | 03/030882 A1 | 4/2003 |
| WO | 2007/030754 A2 | 3/2007 |

OTHER PUBLICATIONS

European Search Report issued in Application No. 12005125.5 dated Oct. 25, 2012.

* cited by examiner

*Primary Examiner* — Susan Tran
(74) *Attorney, Agent, or Firm* — Sughrue Mion, PLLC

(57) ABSTRACT

Provided is a jelly preparation which enables easy intraoral dissolution thereof, easy adjustment of the dissolution time, and stable containment of a drug therein. The jelly preparation of the present invention is a jelly preparation including water, a gelatin, a drug, and a trivalent metal ion.

5 Claims, No Drawings

JELLY-FORM PREPARATION AND METHOD FOR PRODUCING JELLY-FORM PREPARATION

CROSS REFERENCE TO RELATED APPLICATION

This application claims priority from JP 2011-154897 filed Jul. 13, 2011, the contents of which are incorporated herein by reference in their entirety.

TECHNICAL FIELD

The present invention relates to a drug-containing jelly preparation which intraorally dissolves, and a method of producing the jelly preparation.

BACKGROUND ART

Drugs intended for oral administration in the current market include uncoated tablets, coated tablets, capsules, powders, granules, liquids, and the like. With respect to preparations intended to be disintegrated intraorally and absorbed in an alimentary canal, intraorally disintegrating tablets and fast-dissolving intraoral films have already been marketed.

Such a dosage form is focused on in which a drug is taken by intraorally disintegrating or dissolving the drug only with saliva and without chewing the drug because this dosage form improves benefits of patients and caregivers. This is due to an increase in the number of patients with disability in ingestion of food and drink, in other words, those having difficulty in mastication and swallowing, involving an increase in the old people population. In addition, the Silver Science Kenkyu Houkoku (Silver Science research report) of the former Ministry of Welfare (the present Ministry of Health, Labor and Welfare) named "Koreisha ni toyosaiteki na shinkiseizai oyobi shinkihosoyoki no sakuseikenkyu" (Research of producing an optimal new preparation and packaging container for medicating elderly people), 1988, Masayasu SUGIHARA et al. reported that semisolid formulations (e.g. jelly, yogurt, and pudding) are the expected dosage form of drugs in the future.

The aforementioned backgrounds urge recent development of pharmaceutical jelly preparations, and some kinds of products have been already in the market in Japan.

All of these jelly preparations, however, are of portion-packaged type taken with a spoon or the like tools, or of pillow-packaged type taken by pushing it out from the package. Further, the jelly itself is not intraorally dissolved although it is easily dispersed by physical force upon swallowing.

Examples of water-containing jelly-like preparations disclosed so far include jelly preparations containing carrageenan, locust bean gum, and polyacrylic acid or its partially neutralized product or its salt (see Patent Literature 1); and pharmaceutical jelly compositions containing a jelly base and an alkaline salt (see Patent Literature 2).

These jelly preparations, however, contain a gelling agent thermoreversible at high temperatures (about 60° C. to 100° C.) or contain an irreversible gelling agent which is prepared by cross-linking a gelling agent. In other words, the jelly preparations themselves are not intraorally dissolved but easily dispersed by physical force upon swallowing.

For this reason, these conventional jelly preparations require heating at high temperatures upon preparation or contain a metal salt as a cross-linking agent. Thus, poor stability thereof may be a problem particularly in the case that the preparations contain drugs having poor heat stability or proteins or peptides strongly interacting with metal salts.

In addition, film-shaped preparations are known in which a drug is dispersed or dissolved in a water-soluble polymer, as disclosed in Patent Literatures 3, 4, and the like.

These conventional film-shaped preparations intraorally dissolve or swell by a water-soluble polymer. However, these preparations require a certain amount of saliva for the intraoral dissolution or swell, and therefore patients with dysphagia may require much time for dissolving the preparation.

Further, these film-shaped preparations easily absorb water, so that they easily stick to patient's oral mucosa and cause uncomfortable feeling. Particularly in the case of intraorally dissolvable film-shaped preparations, the solubility, film thickness, and size correlate with each other. As a result, they are difficult to contain a drug in an amount exceeding 100 mg.

Furthermore, with respect to a method of producing such film-shaped preparations, a method is disclosed in which a water-soluble polymer is dissolved in water as a solvent, a drug is dissolved in this aqueous solution, and then the solution is heat-dried to produce a preparation. Particularly in the case of less heat-resistant drugs, however, reduction in an amount of the drug by heat is feared.

In the case of liquid drugs, film-shaped preparations may be dissolved, so that a prescribed shape may not be maintained.

CITATION LIST

Patent Literature

Patent Literature 1: JP-A 09-187233
Patent Literature 2: JP-A 2004-99558
Patent Literature 3: JP-T 2005-511522
Patent Literature 4: JP-T 2009-507854

SUMMARY OF INVENTION

Technical Problem

Under the above circumstances, the present invention aims to provide a jelly preparation which enables easy intraoral dissolution, easy adjustment of dissolution time, and stable containment of a drug, and a method of producing the jelly preparation.

Solution to Problem

The present inventors have performed various studies in order to solve the above problems. As a result, they have found that a jelly preparation with heat resistance can be prepared by using, as a base, a gelatin which is gelatinized at normal temperature to keep its solid state, easily dissolves at around body temperature, and contributes to stabilization of heat-sensitive drugs, and by making the base include a trivalent metal ion. Furthermore, they have found that the jelly preparation has a characteristic suitable for intraoral (including sublingual) administration of drugs by optionally containing specific additives which enable preparation of a jelly preparation having physical properties without problems in use. Finally, the present inventors have completed the present invention.

That is, the present invention relates to a jelly preparation including water, a gelatin, a drug, and a trivalent metal ion.

In the jelly preparation of the present invention, the gelatin preferably includes a gelatin derived from porcine, and a gelatin content thereof is preferably 10 to 50% by weight of the whole amount of the jelly preparation.

In the jelly preparation of the present invention, a moisture content is preferably 5 to 90% by weight of the whole amount of the jelly preparation.

Also, the trivalent metal ion is preferably an aluminum ion.

In addition, the jelly preparation of the present invention preferably has a thickness within a range of 30 to 5,000 μm and preferably has a plane area within a range of 0.5 to 6.0 cm$^2$.

Furthermore, the present invention relates to a method of producing the jelly preparation of the present invention. The method includes the steps of mixing water, a gelatin, a drug, and a trivalent metal ion to prepare a mixed solution, and forming a thin film from the mixed solution, wherein an amount of additive water is adjusted in the step of preparing a mixed solution, or a moisture content is adjusted by drying the thin film after the step of forming a thin film.

The present invention will be described in the following.

The jelly preparation of the present invention includes water, a gelatin, a drug, and a trivalent metal ion.

The jelly preparation with such a composition is suitably used for an application wherein a drug is absorbed via oral mucosa and sublingual and for oral desensitization therapy which requires control of sensitization time, and particularly for sublingual desensitization therapy. Also, the jelly preparation of the present invention can significantly improve physical properties in use by including a gelatin and a specific stabilizer.

The jelly preparation of the present invention may have any shape, and an optimum shape thereof depends on its jelly strength and its use. For example, in the case that the composition is used as a jelly preparation taken by patients or care-receivers by themselves, the edible jelly composition preferably has a strength to the extent that the preparation can sufficiently keep its shape, and is preferably a tablet, film, or sheet-form preparation. From the viewpoint of intraoral solubility, in particular, the preparation preferably has a film or sheet shape and, in this case, the thickness is preferably 30 to 5,000 μm. A product with the thickness of less than 30 μm may be poor in film strength and handleability of the product, whereas a product with the thickness of more than 5,000 μm may cause uncomfortable feeling when administered intraorally, especially sublingually.

In the case of using the jelly preparation of the present invention as a sheet-shaped preparation, its plane area is preferably from 0.5 to 6.0 cm$^2$. A preparation with a plane area of smaller than 0.5 cm$^2$ may be difficult for a person to pick up and administer the preparation, whereas a preparation with a plane area of larger than 6.0 cm$^2$ may not be entirely administered intraorally, especially sublingually.

The jelly preparation may have any plane shape, and examples thereof include rectangular shapes such as a rectangle and a square, polygonal shapes such as a pentagon, a circle, an ellipse, and any other shapes. The polygonal shapes herein include not only perfect polygons but also those with slight R at its corner portions.

The jelly preparation of the present invention includes a gelatin.

The gelatin serves as a part of the base of the jelly preparation of the present invention, has sheet-shape forming ability, and is an edible polymer.

As such a gelatin is included, the jelly preparation of the present invention can be gelatinized at normal temperature and can be easily dissolved at around intraoral temperature.

Also, gelatin is gelatinized at the lowest temperature among the thermoreversible gelling agents. Further, it enables to produce a preparation at from normal temperature to around 40° C., and therefore the stability of a drug which is unstable to heat can be secured upon production.

The term "edible" herein means that a preparation is allowed to be orally administered and is pharmaceutically acceptable.

Examples of the gelatin used for the jelly preparation of the present invention include a gelatin obtainable by decomposing and extracting proteins contained in skin or bone of animals using enzymes. Any gelatin obtained by acid-treating or alkali-treating proteins derived from porcine, bovine, and fish can be used.

The above gelatin is preferably a fish-derived or porcine-derived gelatin that can be processed at normal temperature upon production from the viewpoint of stability of a drug which is unstable to heat upon production. Furthermore, in terms of heat resistance of jelly property during storage, porcine-derived gelatins such as a porcine skin-derived gelatin and a porcine bone-derived gelatin are preferable, and these may be processed by acid-treating or alkali-treating. Among these, a porcine bone-derived gelatin is preferable in terms of practicability and stability during storage at around 30° C.

A fish-derived gelatin is also preferable by the same reason in the case that the gelatin includes water in an amount of 20 to 40% by weight of the whole amount of the jelly preparation of the present invention.

The gelatin content of the jelly preparation of the present invention is appropriately determined depending on the kind of the gelatin used. For example, in the case that the gelatin is derived from porcine, the gelatin content is preferably 10 to 50% by weight, and more preferably 20 to 50% by weight, of the whole amount of the jelly preparation of the present invention. If the gelatin content is less than 10% by weight, the jelly preparation of the present invention may not have sufficient heat resistance, and the porcine-derived gelatin may not be gelatinized at normal temperature. If the gelatin content is more than 50% by weight, the jelly preparation of the present invention has extremely slow intraoral solubility, likely resulting in a problem in use.

In the case where the porcine-derived gelatin is used, the moisture content of the jelly preparation of the present invention is preferably 5 to 90% by weight, and more preferably 5 to 80% by weight, of the whole amount of the jelly preparation. If the moisture content is less than 5% by weight, the jelly preparation of the present invention has extremely slow intraoral solubility, likely resulting in a problem in use. If the moisture content is more than 90% by weight, the jelly preparation of the present invention may not have sufficient heat resistance.

Furthermore, in the case that the fish-derived gelatin is used, the amount of the gelatin is preferably 20 to 50% by weight, and more preferably 30 to 50% by weight, of the whole amount of the jelly preparation of the present invention. If the amount is less than 20% by weight, the jelly preparation of the present invention may not have sufficient heat resistance, and the fish-derived gelatin may not be gelatinized at normal temperature. If the amount is more than 50% by weight, the jelly preparation of the present invention has extremely slow intraoral solubility, likely resulting in a problem in use.

In the case of using the fish-derived gelatin as the above gelatin, the jelly preparation of the present invention has inferior heat resistance compared to the case of using the porcine-derived gelatin. The jelly preparation using the fish-derived gelatin, however, can obtain similar heat resistance to that of the preparation using the porcine-derived gelatin by an appropriate adjustment of the amount of the fish-derived gelatin within the above mentioned range.

In addition, the jelly preparation using the fish-derived gelatin can show equal heat resistance to that of the preparation using the porcine-derived gelatin by an adjustment of the moisture content of the jelly preparation of the present invention via drying treatment thereon upon production.

In the case that the fish-derived gelatin is used, the moisture content of the jelly preparation of the present invention is preferably 5 to 80% by weight, and more preferably 5 to 70% by weight, of the whole amount of the jelly preparation. If the moisture content is less than 5% by weight, the jelly preparation of the present invention has extremely slow intraoral solubility, likely resulting in a problem in use. If the moisture content is more than 80% by weight, the jelly preparation of the present invention may not have sufficient heat resistance.

The jelly preparation of the present invention may include an appropriate amount of an edible polymer soluble only in water or an edible polymer soluble neither in water nor in organic solvents (hereinafter, these edible polymers are grouped and referred to as other edible polymers) coupled with the edible polymer of the gelatin to the extent that the effects of the present invention are not inhibited.

Examples of the other edible polymers include: synthetic polymer compounds such as polyethylene glycol, polyvinyl alcohol, a carboxy vinyl polymer, hydroxypropyl methyl cellulose, hydroxyethyl cellulose, methyl cellulose, ethyl cellulose, hydroxypropyl cellulose with a low degree of substitution, crystalline cellulose, carboxymethyl cellulose sodium, carboxymethyl cellulose calcium, carboxymethyl cellulose, and carboxymethyl starch sodium; and polymer compounds obtainable from natural products such as dextran, casein, guar gum, xanthan gum, tragacanth gum, acacia gum, gum arabic, gellan gum, and starch. One of these other edible polymers may be used independently, or two or more of them may be used in combination.

The amount of the other edible polymer(s) is preferably 0.1 to 10% by weight of the whole amount of the jelly preparation of the present invention.

The jelly preparation of the present invention includes a trivalent metal ion.

The trivalent metal ion contributes to improvement of physical properties (such as intraoral solubility) and heat resistance of the jelly preparation of the present invention because the trivalent metal ion composes a three dimensional cross-linked structure. In other words, by adding an additive including the trivalent metal ion, the trivalent metal ion is bound to polypeptide chains of the gelatin to form a three dimensional cross-linked structure. Thereby, the gel structure of the gelatin obtains better intensity, and thus physical properties and heat resistance of the jelly preparation of the present invention are considered to be improved.

Examples of the usable trivalent metal ion include an aluminum ion ($Al^{3+}$), a trivalent iron ion ($Fe^{3+}$), a chromium ion ($Cr^{3+}$), and an indium ion ($In^{3+}$). As the jelly preparation is intended for medical use, an aluminum ion included in alum or a trivalent iron ion included in ferric chloride, both of which have been medically used, is preferably used. Among these, an aluminum ion is preferably used, and an aluminum ion is particularly preferred when the fish-derived gelatin is used as the above gelatin.

Whereas, monovalent metal ions and divalent metal ions cannot improve physical properties and heat resistance of the jelly preparation. This reason is considered that monovalent metal ions and divalent metal ions cannot compose a three dimensional cross-linked structure in the jelly preparation.

The amount of the trivalent metal ion in the jelly preparation of the present invention is preferably 0.01 to 0.15% by weight, and more preferably 0.02 to 0.10% by weight, of the whole amount of the jelly preparation of the present invention. If the amount is less than 0.01% by weight, cross-linking effects brought by the trivalent metal ion may not be exerted. If the amount is more than 0.15% by weight, the jelly preparation of the present invention has extremely slow intraoral solubility, likely resulting in a problem in use.

The jelly preparation of the present invention includes a drug.

The drug is not particularly limited, and the examples thereof include a drug which can be administered to mammals, such as human, sublingually, intraorally, or intraintestinally, that is, a drug which can be orally administered. Specific examples of such a drug include general anesthetics, sedative hypnotics, antiepileptic drugs, antipyretic-analgesic-antiinflammatory drugs, anti-vertiginous drugs, psychoneurotic drugs, central-nervous-system drugs, antidementia drugs, local anesthetics, skeletal muscle relaxants, autonomic-nervous-system drugs, antispasmodics, antiparkinson drugs, antihistamines, cardiotonics, antiarrhythmic drugs, diuretics, hypotensive agents, vasoconstrictors, coronary vasodilators, peripheral vasodilators, antiarteriosclerotic drugs, circulatory-system drugs, respiratory stimulants, cough suppressants and expectorants, hormone drugs, external preparations for purulent diseases, analgesic-antipruritic-astringent-antiphlogistic drugs, drugs for parasitic skin diseases, hemostatics, gout remedies, antidiabetic drugs, antineoplastics, antibiotics, chemotherapeutic drugs, narcotic drugs, smoking cessation aids, and vaccines.

The drug can be included with an amount enough to give a desired result in treatment of diseases, conditions, or disorders, for example, a desired treatment result; such an amount is called an effective amount herein. The term "drug in an effective amount" herein means, for example, a drug in an amount which causes no toxicity but is enough to give a selected effect for a predetermined period. Such an amount can be easily determined by the skilled person.

The drug may be a solid drug or may be a liquid drug. The term "solid drug" herein means a drug which is in a solid state at room temperature (25° C.), that is, a drug having a melting point higher than 25° C. The term "melting point" herein means a value measured using a DSC, model DSC 6220 (Seiko Instruments Inc. (SII)).

The term "liquid drug" herein means a drug having fluidity at room temperature (25° C.), that is, a drug having a viscosity of 0.05 to 100,000 mPa·s at room temperature (25° C.). The viscosity of the drug means a value measured using an E-type viscometer while the temperature of the drug is kept at 25° C.

The amount of the drug depends on its properties, and is generally $1 \times 10^{-10}$ to 80% by weight of the whole amount of the jelly preparation of the present invention. If the drug content is lower than $1 \times 10^{-10}$% by weight, many drugs may not show their efficacy in terms of the clinical effects. If the drug content is higher than 80% by weight, the intensity of the jelly preparation may be extremely deteriorated and the preparation may have a problem in its shape retentivity. The more preferable amount of the drug is $1 \times 10^{-6}$ to 50% by weight. Within the above range of the amount thereof, a jelly preparation without problems in the production and practical use can be prepared.

The jelly preparation of the present invention includes water. The water helps dissolution of the jelly preparation of the present invention. The dissolution time of the jelly preparation of the present invention can be easily adjusted by adjusting the amount of the water in the jelly preparation of the present invention. Therefore, the jelly preparation of the present invention is suitable for both of a case that the preparation is dissolved intraorally to be administered and a case that the preparation is slowly dissolved intraorally, especially sublingually, to sustain-release a drug.

The amount of the water is preferably 1 to 60% by weight, and more preferably 5 to 50% by weight, of the whole amount of the jelly preparation of the present invention. If the amount thereof is less than 1% by weight, intraoral solubility is extremely poor, likely resulting in a problem in use. If the amount is more than 60% by weight, storage stability in terms of physical properties at normal temperature may be poor.

The jelly preparation of the present invention may further contain an additive which improves the physical properties and solubility. Examples of the additive include saccharides, alcohols of saccharides, and sugar fatty acids Examples of the saccharides include the following monosaccharides, disaccharides, and tri- to hexa-saccharides.

Examples of the monosaccharides include: aldotetroses such as erythrose and threose; aldopentoses such as ribose, lyxose, xylose, and arabinose; aldohexoses such as allose, talose, gulose, glucose, altrose, mannose, galactose, and idose; ketotetroses such as erythrulose; ketopentoses such as xylulose and ribulose; and ketohexoses such as psicose, fructose, sorbose, and tagatose. Examples of the disaccharides include: α-diglucosides such as trehalose, kojibiose, nigerose, maltose, and isomaltose; β-diglucosides such as isotrehalose, sophorose, laminaribiose, cellobiose, and genthiobiose; and α,β-diglucosides such as neotrehalose, as well as lactose, sucrose, and isomaltulose (palatinose). Examples of the trisaccharides include raffinose. Examples of the tri- to hexa-oligosaccharides include fructooligosaccharide, galactooligosaccharide, xylooligosaccharide, isomaltooligosaccharide, chitin oligosaccharide, chitosan oligosaccharide, oligoglucosamine, dextrin, and cyclic oligosaccharides such as cyclodextrin.

Examples of alcohols of the monosaccharides include tetritols such as erythritol, D-threitol, and L-threitol; pentitols such as D-arabinitol and xylitol; hexitols such as D-iditol, galactitol (dulcitol), D-glucitol (sorbitol), and mannitol; and cyclitols such as inositol. Examples of alcohols of the disaccharides include maltitol, lactitol, and reduced palatinose (isomalt). Examples of alcohols of the oligosaccharides include pentaerythritol and reduced maltose syrup.

In the jelly preparation of the present invention, the saccharides or alcohols of the saccharides may be optionally substituted, and each of these may be used alone or two or more of these may be used in admixture.

The saccharides or alcohols of the saccharides are preferably mono- to tri-saccharides or alcohols of these saccharides in order to easily dissolve the jelly preparation of the present invention intraorally and to prevent a great change in viscosity of the solution in the production process.

Examples of the sugar fatty acids include sorbitan fatty acid esters and sucrose fatty acid esters.

Examples of the sorbitan fatty acid esters include sorbitan monooleate, sorbitan trioleate, sorbitan sesquioleate, sorbitan cocoate, and polyoxyethylene sorbitan fatty acid esters.

Examples of the sucrose fatty acid esters include sucrose stearate, sucrose oleate, sucrose palmitate, sucrose myristate, sucrose behenate, sucrose erucate, and sucrose-mixed fatty acid esters.

These sugar fatty acids are very advantageous because the sugar fatty acids work as antifoaming agents in addition to work as stabilizers for proteins and peptides.

The amount of the additive of the jelly preparation of the present invention is preferably 1 to 80% by weight, and more preferably 5 to 70% by weight, of the whole amount of the jelly preparation of the present invention. If the amount is less than 1% by weight, sufficient physical properties may not be secured in its use. If the amount is more than 80% by weight, it may be difficult to control the physical properties of the jelly preparation of the present invention because of the additive.

In addition, the jelly preparation of the present invention may appropriately contain other components such as perfumes, flavoring agents, sweetening agents, coloring agents, antiseptics, antioxidants, stabilizing agents, surfactants, and antifoaming agents, if necessary, as components constituting the base of the jelly preparation. The materials thereof are not particularly limited, and known materials may be used.

Since the jelly preparation of the present invention includes the gelatin as mentioned above, the preparation can be gelatinized at normal temperature and can be easily dissolved at around intraoral temperature. Moreover, the physical properties in use can be significantly improved by inclusion of the gelatin and specific additives. Also, the jelly preparation of the present invention can easily adjust its dissolution time by adjusting the addition amount of the trivalent metal ion or the moisture content. Therefore, the preparation is suitable for drugs absorbed via oral mucosa and sublingual mucosa and for oral desensitization therapy which requires control of sensitization time, and particularly for sublingual desensitization therapy.

The jelly preparation of the present invention may naturally be swallowed as it is, or may be rapidly dissolved intraorally and then swallowed. In addition, the intraoral dissolution time is adjustable, and thus the preparation can be expected to be absorbed through the oral mucosa and sublingual mucosa. Since the preparation can be perfectly dissolved at body temperature and thus causes no feeling of residues, and since the preparation has a sheet shape and the surface area thereof is larger than tablets and the like, whereby patients and caregivers can easily pick it up with their fingers, the jelly preparation of the present invention can greatly improve the QOL of patients and caregivers.

The jelly preparation of the present invention can be produced, for example, by the steps of preparing a mixed solution by mixing water, a gelatin, a drug, and a trivalent metal ion, and forming a thin film from the mixed solution, wherein an amount of additive water is adjusted in the step of preparing a mixed solution, or a moisture content is adjusted by drying the thin film after the step of forming a thin film. Such a method of producing the jelly preparation of the present invention is also one aspect of the present invention.

In the step of preparing a mixed solution, the mixed solution is prepared according to the following, for example. A gelatin, a trivalent metal ion, and other additives are added to a prescribed moisture content and dissolved at normal temperature or by heating. Insoluble additives are dispersed into the resulting solution to prepare a gelatin solution. In the case that the drug is stable to heat, the drug may be added at this stage to prepare a mixed solution. In the case that the drug is unstable to heat, the drug is added after the gelatin solution is cooled down to normal temperature to around 35° C., and then the solution is stirred and mixed to prepare a mixed solution.

If foams appear during preparation of the mixed solution, the solution may be left for a night, vacuumed, or decompressed for defoaming.

In the step of forming a thin film, for example, the prescribed amount of the mixed solution is dispensed into a plastic blister case with a desired size at 28° C. to 35° C., and the mixed solution is cooled and solidified immediately after the dispensation to form a thin film. Instead of the dispensing step, an alternative method may be employed in which an appropriate amount of the mixed solution is applied to a plastic release film, the applied solution is cooled and solidified to form a thin film, and then the film is cut into pieces each having a desired size.

The thin film formed in this step preferably has an equal size to that of the jelly preparation of the present invention.

According to the method of producing the jelly preparation of the present invention, the moisture content of the jelly preparation to be obtained is adjusted by adjusting the amount of additive water in the step of preparing a mixed solution, or the moisture content of the jelly preparation to be obtained is adjusted by drying the thin film after the step of forming a thin film.

In other words, in the case that the adjustment of the moisture content is performed in the step of preparing a mixed solution, the jelly preparation of the present invention may be produced by forming the thin film.

In the case that the adjustment of the moisture content is performed by drying the thin film after the step of forming a thin film, the jelly preparation of the present invention may be produced by drying the thin film.

The thin film may be dried by cold air drying process or cold vacuum drying process, for example.

The moisture content is preferably adjusted so that the moisture content of the jelly preparation to be obtained equals to the moisture content, as described above, of the jelly preparation of the present invention.

The method of producing the jelly preparation of the present invention is very useful in the point that drugs particularly unstable to heat can be processed at a low temperature of 35° C. or lower, or preferably 30° C. or lower.

Preferably, the obtained jelly preparation is airtightly packed if necessary and thereby prepared as products.

Advantageous Effects of Invention

Since the jelly preparation of the present invention contains a gelatin, the preparation can be gelatinized at normal temperature, and can be easily dissolved at around intraoral temperature. Also, since the dissolution time can be easily adjusted by adjusting the addition amount of the trivalent metal ion or the moisture content in the jelly preparation, the sheet-shaped preparation of the present invention is suitable for drugs absorbed via oral mucosa and sublingual mucosa and for oral desensitization therapy which requires control of sensitization time, and particularly for sublingual desensitization therapy. In addition, since the jelly preparation of the present invention contains the gelatin and the specific additives, the physical properties in use can be significantly improved.

Furthermore, the jelly preparation of the prevent invention may naturally be swallowed as it is, or may be rapidly dissolved intraorally and then swallowed. In addition, the intraoral dissolution time is adjustable, and thus the composition can be expected to be absorbed through the oral mucosa and sublingual mucosa. Since the preparation can be perfectly dissolved at body temperature and thus causes no feeling of residues. Furthermore, since the preparation has a sheet shape and the surface area thereof is larger than tablets and the like, which enables patients and caregivers to easily pick it up with their fingers, the jelly preparation can greatly improve the QOL of patients and caregivers.

Moreover, the method of producing the jelly preparation of the present invention uses a gelatin which can be prepared at a lower temperature than that of the preparation of conventional thermoreversible gelling agents. Therefore, the method enables production of the jelly preparation containing a drug unstable to heat, while reducing loss in the drug content.

DESCRIPTION OF EMBODIMENTS

The following description is given to illustrate the present invention by way of examples, but the present invention is not limited to these examples.

Examples 1 to 3

To 40 parts by weight of purified water was added 0.1 parts by weight each of Polysorbate 80 and medium chain triglycerides (MCTG, Coconad Mont., from Kao Corporation) as defoaming agents, and 0.1 parts by weight of p-hydroxybenzonate methyl(methylparaben) as an antiseptic. The mixture was ultrasonically dissolved and dispersed. To the obtained solution, alum (aluminum potassium sulfate hydrate from Wako Pure Chemical Industries, Ltd.) (the aluminum content thereof is about 5.7% by weight of the whole alum amount) with the amount (parts by weight) shown in Table 1 was added and dissolved. To the resulting solution was added 10 parts by weight of porcine bone gelatin (AEP, from Nippi Inc.), and the gelatin was dissolved at 30° C. to 40° C. A 1 gram portion of the solution was dispensed to a 5 $cm^2$ plastic blister case (Cryomold (square type) No. 3, from Sakura Finetek Japan Co., Ltd.), and cooled and solidified at 2° C. to 8° C. overnight. In this manner, a jelly composition was provided.

Examples 4 to 12

Jelly compositions were provided in the same manner as in Examples 1 to 3, except that ingredients were prepared according to Table 1.

An acid-treated porcine skin-derived gelatin (AP-200F, from Nippi Inc.) was used in Examples 4 to 6, an alkali-treated porcine skin-derived gelatin (BP-200F, from Nippi Inc.) was used in Examples 7 to 9, and a water-soluble porcine skin-derived gelatin (CS, from Nippi Inc.) was used in Examples 10 to 12.

Comparative Example 1

To 40 parts by weight of purified water was added 0.1 parts by weight each of Polysorbate 80, medium chain triglycerides (MCTG), and methylparaben. The mixture was ultrasonically dissolved and dispersed. To the obtained solution was added 10 parts by weight of a porcine bone gelatin (AEP, from Nippi Inc.), and the gelatin was dissolved at 30° C. to 40° C. A 1 gram portion of the solution was dispensed to a 5 $cm^2$ plastic blister case (Cryomold (square type) No. 3), and cooled and solidified at 2° C. to 8° C. overnight. In this manner, a jelly composition was provided.

Comparative Examples 2 to 4

Jelly compositions were provided in the same manner as in Comparative Example 1, except that ingredients were prepared according to Table 2.

Comparative Example 5

To 40 parts by weight of purified water was added 0.1 parts by weight of methylparaben. The mixture was ultrasonically dissolved and dispersed, and 0.1 parts by weight of alum was added thereto and dissolved. To the obtained solution was added 10 parts by weight of agar, and the agar was dissolved at 80° C. to 90° C. A 1 gram portion of the solution was dispensed to a 5 $cm^2$ plastic blister case (Cryomold (square type) No. 3), and cooled and solidified at 2° C. to 8° C. overnight. In this manner, a jelly composition was provided.

Comparative Examples 6 and 7

Jelly compositions were provided in the same manner as in Comparative Example 5, except that ingredients were prepared according to Table 2.

Examples 13 to 24

Jelly compositions were provided in the same manner as in Examples 1 to 3, except that ingredients were prepared according to Table 3.

TABLE 1

| Ingredient | Example [parts by weight] | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Porcine bone gelatin | 10 | 10 | 10 | — | — | — | — | — | — | — | — | — |
| Acid-treated porcine gelatin | — | — | — | 10 | 10 | 10 | — | — | — | — | — | — |
| Alkali-treated porcine gelatin | — | — | — | — | — | — | 10 | 10 | 10 | — | — | — |
| Water-soluble porcine gelatin | — | — | — | — | — | — | — | — | — | 10 | 10 | 10 |
| Alum | 0.1 | 0.3 | 0.5 | 0.1 | 0.3 | 0.5 | 0.1 | 0.3 | 0.5 | 0.1 | 0.3 | 0.5 |
| Polysorbate 80 | 0.1 | 0.1 | 0.1 | 0.1 | 0.1 | 0.1 | 0.1 | 0.1 | 0.1 | 0.1 | 0.1 | 0.1 |
| MCTG | 0.1 | 0.1 | 0.1 | 0.1 | 0.1 | 0.1 | 0.1 | 0.1 | 0.1 | 0.1 | 0.1 | 0.1 |
| Methylparaben | 0.1 | 0.1 | 0.1 | 0.1 | 0.1 | 0.1 | 0.1 | 0.1 | 0.1 | 0.1 | 0.1 | 0.1 |
| Purified water | 40 | 40 | 40 | 40 | 40 | 40 | 40 | 40 | 40 | 40 | 40 | 40 |
| Moisture content [%] | 79.4 | 79.1 | 78.7 | 79.4 | 79.1 | 78.7 | 79.4 | 79.1 | 78.7 | 79.4 | 79.1 | 78.7 |

TABLE 2

| Ingredient | Comparative Example [parts by weight] | | | | | | |
|---|---|---|---|---|---|---|---|
| | 1 | 2 | 3 | 4 | 5 | 6 | 7 |
| Porcine bone gelatin | 10 | — | — | — | — | — | — |
| Acid-treated porcinee gelatin | — | 10 | — | — | — | — | — |
| Alkali-treated porcine gelatin | — | — | 10 | — | — | — | — |
| Water-soluble porcine gelatin | — | — | — | 10 | — | — | — |
| Agar | — | — | — | — | 10 | — | — |
| Locust bean gum | — | — | — | — | — | 10 | — |
| Starch | — | — | — | — | — | — | 10 |
| Alum | — | — | — | — | 0.1 | 0.1 | 0.1 |
| Polysorbate 80 | 0.1 | 0.1 | 0.1 | 0.1 | — | — | — |
| MCTG | 0.1 | 0.1 | 0.1 | 0.1 | — | — | — |
| Methylparaben | 0.1 | 0.1 | 0.1 | 0.1 | 0.1 | 0.1 | 0.1 |
| Purified water | 40 | 40 | 40 | 40 | 40 | 40 | 40 |
| Moisture content [%] | 79.5 | 79.5 | 79.5 | 79.5 | 79.7 | 79.7 | 79.7 |

A bovine gelatin (CP-1045, from JELLICE) was used in Examples 13 to 15, an alkali-treated bovine gelatin (AD4, from Nippi Inc.) was used in Examples 16 to 18, a fish gelatin (FGS-230, from Nippi Inc.) was used in Examples 19 to 21, and a water-soluble fish gelatin (CSF, from Nippi Inc.) was used in Examples 22 to 24.

Comparative Examples 8 to 11

Jelly compositions were provided in the same manner as in Comparative Example 1, except that ingredients were prepared according to Table 3.

TABLE 3

| Ingredient | Example [parts by weight] | | | | | | | | | | | | Comparative Example [parts by weight] | | | |
|---|---|---|---|---|---|---|---|---|---|---|---|---|---|---|---|---|
| | 13 | 14 | 15 | 16 | 17 | 18 | 19 | 20 | 21 | 22 | 23 | 24 | 8 | 9 | 10 | 11 |
| Bovine gelatin | 10 | 10 | 10 | — | — | — | — | — | — | — | — | — | 10 | — | — | — |
| Alkali-treated bovine gelatin | — | — | — | 10 | 10 | 10 | — | — | — | — | — | — | — | 10 | — | — |
| Fish gelatin | — | — | — | — | — | — | 10 | 10 | 10 | — | — | — | — | — | 10 | — |
| Water-soluble fish gelatin | — | — | — | — | — | — | — | — | — | 10 | 10 | 10 | — | — | — | 10 |
| Alum | 0.1 | 0.3 | 0.5 | 0.1 | 0.3 | 0.5 | 0.1 | 0.3 | 0.5 | 0.1 | 0.3 | 0.5 | — | — | — | — |
| Polysorbate 80 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| MCTG | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Methylparaben | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Purified water | 40 | 40 | 40 | 40 | 40 | 40 | 40 | 40 | 40 | 40 | 40 | 40 | 40 | 40 | 40 | 40 |
| Moisture content [%] | 79.4 | 79.1 | 78.7 | 79.4 | 79.1 | 78.7 | 79.4 | 79.1 | 78.7 | 79.4 | 79.1 | 78.7 | 79.5 | 79.5 | 79.5 | 79.5 |

Examples 25 to 28

Jelly compositions were provided in the same manner as in Example 1, except that ingredients were prepared according to Table 4.

Comparative Examples 12 to 15

Jelly compositions were provided in the same manner as in Comparative Example 1, except that ingredients were prepared according to Table 4.

TABLE 4

| Ingredient | Example [parts by weight] | | | | Comparative Example [parts by weight] | | | |
|---|---|---|---|---|---|---|---|---|
| | 25 | 26 | 27 | 28 | 12 | 13 | 14 | 15 |
| Porcine bone gelatin | 15 | 20 | — | — | 15 | 20 | — | — |
| Water-soluble fish gelatin | — | — | 15 | 20 | — | — | 15 | 20 |
| Alum | 0.5 | 0.5 | 0.5 | 0.5 | — | — | — | — |
| Polysorbate 80 | 0.1 | 0.1 | 0.1 | 0.1 | 0.1 | 0.1 | 0.1 | 0.1 |
| MCTG | 0.1 | 0.1 | 0.1 | 0.1 | 0.1 | 0.1 | 0.1 | 0.1 |
| Methylparaben | 0.1 | 0.1 | 0.1 | 0.1 | 0.1 | 0.1 | 0.1 | 0.1 |
| Purified water | 35 | 30 | 35 | 30 | 35 | 30 | 35 | 30 |
| Moisture content [%] | 68.9 | 59.1 | 68.9 | 59.1 | 69.6 | 59.6 | 69.6 | 59.6 |

Examples 29 to 32

Gelatin-containing solutions were prepared in the same manner as in Example 1, except that ingredients were prepared according to Table 5. Each solution was dispensed to a blister case. Then, the blister case was placed in an airtight container with silica gel spread in the bottom, and the solution was cooled and solidified at 2° C. to 8° C. overnight to provide a jelly composition. The composition was measured for the weight and then was further cooled in the airtight container until the amount of the moisture content shown in Table 5 dried off.

Comparative Examples 16 to 19

Gelatin-containing solutions were prepared in the same manner as in Comparative Example 1, except that ingredients were prepared according to Table 5. Each solution was dispensed to a blister case. Then, the blister case was placed in an airtight container with silica gel spread in the bottom, and the solution was cooled and solidified at 2° C. to 8° C. overnight to provide a jelly composition. The composition was measured for the weight and then was further cooled in the airtight container until the amount of the moisture content shown in Table 5 dried off.

Example 33

To 40 parts by weight of purified water was added 0.1 parts by weight each of Polysorbate 80, medium chain triglycerides (MCTG), and methylparaben. The mixture was ultrasonically dissolved and dispersed. To the obtained solution, 50 parts by weight of loxoprofen sodium (from Yoshindo Inc.) and 0.8 parts by weight of alum were added and dissolved. To the resulting solution was added 10 parts by weight of a porcine bone gelatin, and the gelatin was dissolved at 30° C. to 40° C. to prepare a mixed solution. A 1 gram portion of the solution was dispensed to a 5 cm² plastic blister case (Cryomold (square type) No. 3), and cooled and solidified at 2° C. to 8° C. overnight. In this manner, a jelly preparation was provided.

Example 34

To 40 parts by weight of purified water was added 0.1 parts by weight each of Polysorbate 80, medium chain triglycerides (MCTG), and methylparaben. The mixture was ultrasonically dissolved and dispersed. To the obtained solution was added 0.8 parts by weight of alum and the alum was dissolved. To the resulting solution was added 10 parts by weight of a porcine bone gelatin. The gelatin was dissolved at 30° C. to 40° C., and the solution was stirred in a shaker under a constant temperature of 30° C. to 35° C. to prepare a gelatin solution. Separately, 50 parts by weight of human insulin solution (100 units) (Humulin R, 100 units/mL, from Eli Lilly Japan K.K.) was prepared and heated up to 30° C. to 35° C. The whole amount of the heated solution was added to the previously prepared gelatin solution, and these solutions were immediately mixed at 30° C. to 35° C. to prepare a mixed solution. A 1 gram portion of the mixed solution was dispensed to a 5 cm² plastic blister case (Cryomold (square type) No. 3), and cooled and solidified at 2° C. to 8° C. overnight. In this manner, a jelly preparation was provided.

TABLE 5

| Ingredient | Example [parts by weight] | | | | Comparative Example [parts by weight] | | | |
|---|---|---|---|---|---|---|---|---|
| | 29 | 30 | 31 | 32 | 16 | 17 | 18 | 19 |
| Porcine bone gelatin | 10 | 10 | — | — | 10 | 10 | — | — |
| Water-soluble fish gelatin | — | — | 10 | 10 | — | — | 10 | 10 |
| Alum | 0.5 | 0.5 | 0.5 | 0.5 | — | — | — | — |
| Purified water | 40 | 40 | 40 | 40 | 40 | 40 | 40 | 40 |
| Polysorbate 80 | 0.1 | 0.1 | 0.1 | 0.1 | 0.1 | 0.1 | 0.1 | 0.1 |
| MCTG | 0.1 | 0.1 | 0.1 | 0.1 | 0.1 | 0.1 | 0.1 | 0.1 |
| Methylparaben | 0.1 | 0.1 | 0.1 | 0.1 | 0.1 | 0.1 | 0.1 | 0.1 |
| Dried moisture content | [10] | [20] | [10] | [20] | [10] | [20] | [10] | [20] |
| Moisture content [%] | 73.5 | 64.9 | 73.5 | 64.9 | 73.5 | 64.9 | 73.5 | 64.9 |

Example 35

To 40 parts by weight of purified water was added 0.1 parts by weight each of Polysorbate 80, medium chain triglycerides (MCTG), and methylparaben. The mixture was ultrasonically dissolved and dispersed. To the obtained solution, 50 parts by weight of cedar pollen extract (from LSL Co., Ltd.) and 0.8 parts by weight of alum were added and dissolved. To the resulting solution was added 10 parts by weight of a porcine bone gelatin, and the gelatin was dissolved at 30° C. to 35° C. to prepare a mixed solution. A 1 gram portion of the mixed solution was dispensed to a 5 cm$^2$ plastic blister case (Cryomold (square type) No. 3), and cooled and solidified at 2° C. to 8° C. overnight. In this manner, a jelly preparation was provided.

Examples 36 AND 37

Jelly preparations were provided in the same manner as in Example 33, except that ingredients were prepared according to Table 6.

A purified mite antigens Der f I (from Shibayagi Co., Ltd.) was used in Example 36, and a purified mite antigens Der f II (from Shibayagi Co., Ltd.) was used in Example 37.

TABLE 6

| Ingredient | Example [parts by weight] | | | | |
|---|---|---|---|---|---|
| | 33 | 34 | 35 | 36 | 37 |
| Loxoprofen sodium | 50 | — | — | — | — |
| Human insulin solution with 100 units | — | 50 | — | — | — |
| Cedar pollen extract | — | — | 50 | — | — |
| Mite antigens Der f I | — | — | — | 50 | — |
| Mite antigens Der f II | — | — | — | — | 50 |
| Porcine bone gelatin | 10 | 10 | 10 | 10 | 10 |
| Alum | 0.8 | 0.8 | 0.8 | 0.8 | 0.8 |
| Purified water | 40 | 40 | 40 | 40 | 40 |
| Polysorbate 80 | 0.1 | 0.1 | 0.1 | 0.1 | 0.1 |
| MCTG | 0.1 | 0.1 | 0.1 | 0.1 | 0.1 |
| Methylparaben | 0.1 | 0.1 | 0.1 | 0.1 | 0.1 |

[Test Method]

The jelly composition or the jelly preparation in each example and comparative example was evaluated for intraoral solubility, gelation temperature upon preparation, a sensory test (texture), and storage stability (sensory test (texture)) when stored at 25° C.

Some samples were measured for intraoral dissolution time and heat resistance determined from each melting point. Each test method is described below and the results are shown in Tables 7 to 12.

(Measurement of Intraoral Dissolution Time)

A disintegration test was performed according to the 15$^{th}$ revision of Japanese pharmacopoeia. The test was performed under the following condition: Distilled water was placed in a 1000 mL low-type beaker of a test apparatus, and then the test apparatus was reciprocated up and down 29 to 32 times per minute with an amplitude of 53 to 57 mm at a temperature of 37±2° C. The jelly composition or jelly preparation was placed in the test apparatus, and the test was performed under the aforementioned condition. The time period from the start of the test until the jelly composition or jelly preparation was completely dissolved and disappeared in the test apparatus was determined as a dissolution time in the mouth.

(Evaluation of Intraoral Solubility)

To a 1000 mL glass petri dish was added 900 mL of phosphate buffer with a pH of 6.8. To the petri dish, a stainless sieve (φ: 4 mm) was sunk up-side down, and the solution was stirred with a stirrer (300 rpm). The temperature of the solution was controlled at 37±2° C. by a thermostatic water circulator. To the solution, a test specimen (5 cm$^2$) of the jelly composition or jelly preparation was sunk. The solution was left for 10 minutes after the test specimen was sunk. Then, evaluation was conducted to determine whether the specimen remained on the stainless sieve. The evaluation criteria are as follows.

4: No residue is observed.
1: Residue is observed.

(Storage Stability Test)

The prepared jelly composition or jelly preparation was stored in a constant-temperature bath set to 25° C. and taken out of the bath one month after the start of the storage. The composition or preparation was examined by a sensory test (texture) and evaluated. The evaluation method was based on that of a sensory test (texture).

(Sensory Test (Texture))

Sensory test was performed as follows. A specimen was cut from the jelly composition or jelly preparation of each Example and Comparative Example. A tester touched the specimen for five seconds in such a manner that circles were drawn on the specimen surface with a finger, and the specimen was checked if the surface thereof was not sticky and if the finger did not become wet, and evaluated. The evaluation criteria are as follows.

4: The surface is not sticky, and the finger does not become wet.
3: The surface is slightly sticky, or the finger becomes wet.
2: The stickiness of the surface and the wet of the finger cause an uncomfortable feeling.
1: The surface is considerably sticky, and some jelly remains on the finger.

(Gelation Temperature Upon Preparation)

The jelly composition or jelly preparation was evaluated for the temperature at which gelatinization occurred and viscosity suddenly increased during preparation to determine if the production at a low temperature was possible. The evaluation criteria are as follows.

4: below 30° C.
3: 30° C. to below 40° C.
2: 40° C. to below 50° C.
1: 50° C. or above (Heat Resistance)

For evaluation of heat resistance of the jelly composition, the prepared jelly composition or jelly preparation was stored in a constant-temperature bath set to 30° C., and the jelly composition or jelly preparation was taken out of the bath one week, two weeks, and one month, after the start of the storage, and its appearance was evaluated. The evaluation criteria are as follows.

4: No dissolution is observed.
3: A low level of dissolution is observed. The composition does not leak even when the blister is tilted.
2: A middle level of dissolution is observed. The composition slowly leaks when the blister is tilted.
1: A high level of dissolution is observed. The composition promptly leaks when the blister is tilted, or the composition is sol.

TABLE 7

| Sample | During preparation Gelation temperature | After preparation Sensory (Texture) | After preparation Solubility (37° C.) | One month after storage at 25° C. Sensory (Texture) | One month after storage at 25° C. Solubility (37° C.) | Total | Orally dissolution time [sec] |
|---|---|---|---|---|---|---|---|
| Example 1 | 3 | 4 | 4 | 3 | 4 | 18 | 39.3 |
| Example 2 | 3 | 4 | 4 | 4 | 4 | 19 | 75.3 |
| Example 3 | 3 | 4 | 4 | 4 | 4 | 19 | 105.7 |
| Example 4 | 4 | 4 | 4 | 3 | 4 | 19 | 22.7 |
| Example 5 | 4 | 4 | 4 | 4 | 4 | 20 | 47.7 |
| Example 6 | 3 | 4 | 4 | 4 | 4 | 19 | 72.0 |
| Example 7 | 4 | 4 | 4 | 3 | 4 | 19 | 34.0 |
| Example 8 | 3 | 4 | 4 | 4 | 4 | 19 | 61.7 |
| Example 9 | 3 | 4 | 4 | 4 | 4 | 19 | 96.0 |
| Example 10 | 4 | 3 | 4 | 3 | 4 | 18 | 24.3 |
| Example 11 | 4 | 4 | 4 | 3 | 4 | 19 | 28.0 |
| Example 12 | 3 | 4 | 4 | 4 | 4 | 19 | 29.3 |
| Comparative Example 1 | 3 | 3 | 4 | 3 | 4 | 17 | 23.3 |
| Comparative Example 2 | 4 | 3 | 4 | 3 | 4 | 18 | 22.0 |
| Comparative Example 3 | 4 | 3 | 4 | 3 | 4 | 18 | 23.0 |
| Comparative Example 4 | 4 | 3 | 4 | 2 | 4 | 17 | 20.0 |
| Comparative Example 5 | 1 | 4 | 1 | 4 | 1 | 11 | — |
| Comparative Example 6 | 2 | 3 | 1 | 3 | 1 | 10 | — |
| Comparative Example 7 | 2 | 1 | 4 | 1 | 4 | 12 | — |

TABLE 8

| Sample | During preparation Gelation temperature | After preparation Sensory (Texture) | After preparation Solubility (37° C.) | One month after storage at 25° C. Sensory (Texture) | One month after storage at 25° C. Solubility (37° C.) | Total | Orally dissolution time [sec] |
|---|---|---|---|---|---|---|---|
| Example 13 | 3 | 4 | 4 | 3 | 4 | 18 | 46.7 |
| Example 14 | 3 | 4 | 4 | 4 | 4 | 19 | 77.3 |
| Example 15 | 3 | 4 | 4 | 4 | 4 | 19 | 84.7 |
| Example 16 | 3 | 4 | 4 | 3 | 4 | 18 | 45.0 |
| Example 17 | 3 | 4 | 4 | 4 | 4 | 19 | 88.3 |
| Example 18 | 3 | 4 | 4 | 4 | 4 | 19 | 94.0 |
| Example 19 | 4 | 4 | 4 | 2 | 4 | 18 | 16.7 |
| Example 20 | 4 | 4 | 4 | 3 | 4 | 19 | 35.3 |
| Example 21 | 3 | 4 | 4 | 4 | 4 | 19 | 41.3 |
| Example 22 | 4 | 3 | 4 | 2 | 4 | 17 | 14.3 |
| Example 23 | 4 | 4 | 4 | 3 | 4 | 19 | 33.3 |
| Example 24 | 3 | 4 | 4 | 4 | 4 | 19 | 45.3 |
| Comparative Example 8 | 3 | 3 | 4 | 3 | 4 | 17 | 32.3 |
| Comparative Example 9 | 3 | 3 | 4 | 3 | 4 | 17 | 24.0 |
| Comparative Example 10 | 4 | 3 | 4 | 2 | 4 | 17 | 15.3 |
| Comparative Example 11 | 4 | 2 | 4 | 2 | 4 | 16 | 12.0 |

TABLE 9

| Sample | During preparation Gelation temperature | After preparation Sensory (Texture) | After preparation Solubility (37° C.) | One month after storage at 25° C. Sensory (Texture) | One month after storage at 25° C. Solubility (37° C.) | Total | Orally dissolution time [sec] |
|---|---|---|---|---|---|---|---|
| Comparative Example 12 | 3 | 4 | 4 | 4 | 4 | 19 | 33.0 |
| Comparative Example 13 | 3 | 4 | 4 | 4 | 4 | 19 | 156.7 |
| Example 25 | 3 | 4 | 4 | 4 | 4 | 19 | 101.7 |

TABLE 9-continued

| Sample | During preparation Gelation temperature | After preparation Sensory (Texture) | After preparation Solubility (37° C.) | One month after storage at 25° C. Sensory (Texture) | One month after storage at 25° C. Solubility (37° C.) | Total | Orally dissolution time [sec] |
|---|---|---|---|---|---|---|---|
| Example 26 | 3 | 4 | 4 | 4 | 4 | 19 | 619.7 |
| Comparative Example 14 | 4 | 3 | 4 | 3 | 4 | 18 | 16.0 |
| Comparative Example 15 | 3 | 4 | 4 | 3 | 4 | 18 | 49.7 |
| Example 27 | 4 | 4 | 4 | 4 | 4 | 20 | 54.7 |
| Example 28 | 3 | 4 | 4 | 4 | 4 | 19 | 128.3 |

TABLE 10

| Sample | During preparation Gelation temperature | After preparation Sensory (Texture) | After preparation Solubility (37° C.) | One month after storage at 25° C. Sensory (Texture) | One month after storage at 25° C. Solubility (37° C.) | Total | Orally dissolution time [sec] |
|---|---|---|---|---|---|---|---|
| Comparative Example 16 | 3 | 4 | 4 | 3 | 4 | 18 | 29.7 |
| Comparative Example 17 | 3 | 4 | 4 | 4 | 4 | 19 | 36.0 |
| Example 29 | 3 | 4 | 4 | 4 | 4 | 19 | 262.3 |
| Example 30 | 3 | 4 | 4 | 3 | 4 | 18 | 766.3 |
| Comparative Example 18 | 4 | 4 | 4 | 4 | 4 | 20 | 15.3 |
| Comparative Example 19 | 4 | 4 | 4 | 4 | 4 | 20 | 21.0 |
| Example 31 | 4 | 4 | 4 | 2 | 4 | 18 | 104.3 |
| Example 32 | 4 | 4 | 4 | 3 | 4 | 19 | 290.7 |

TABLE 11

| Sample | Heat resistance after storage at 30° C. 1 W | Heat resistance after storage at 30° C. 2 W | Heat resistance after storage at 30° C. 1 M |
|---|---|---|---|
| Example 3 | 4 | 4 | 4 |
| Example 6 | 4 | 3 | 1 |
| Example 9 | 4 | 4 | 3 |
| Comparative Example 1 | 1 | — | — |
| Comparative Example 2 | 1 | — | — |
| Comparative Example 3 | 1 | — | — |
| Example 25 | 4 | 4 | 4 |
| Example 26 | 4 | 4 | 4 |
| Comparative Example 12 | 2 | 2 | 1 |
| Comparative Example 13 | 3 | 3 | 2 |
| Example 27 | 2 | 2 | 1 |
| Example 28 | 4 | 4 | 3 |
| Comparative Example 14 | 1 | 1 | — |
| Comparative Example 15 | 2 | 2 | 1 |
| Example 29 | 4 | 4 | 4 |
| Example 30 | 4 | 4 | 4 |
| Comparative Example 16 | 1 | — | — |
| Comparative Example 17 | 2 | 1 | — |
| Example 31 | 3 | 3 | 2 |
| Example 32 | 4 | 4 | 4 |
| Comparative Example 18 | 1 | — | — |
| Comparative Example 19 | 1 | — | — |

TABLE 12

| Sample | During preparation Gelation temperature | After preparation Sensory (Texture) | After preparation Solubility (37° C.) | One month after storage at 25° C. Sensory (Texture) | One month after storage at 25° C. Solubility (37° C.) | Total | Orally dissolution time [sec] |
|---|---|---|---|---|---|---|---|
| Example 33 | 4 | 4 | 4 | 4 | 4 | 20 | 70.2 |
| Example 34 | 4 | 4 | 4 | 4 | 4 | 20 | 63.7 |
| Example 35 | 4 | 4 | 4 | 4 | 4 | 20 | 76.2 |
| Example 36 | 4 | 4 | 4 | 4 | 4 | 20 | 73.4 |
| Example 37 | 4 | 4 | 4 | 4 | 4 | 20 | 74.8 |

As shown in Tables 7 to 12, the jelly compositions and jelly preparations according to examples obtained good results in all evaluation items. On the other hand, the jelly compositions and jelly preparations according to comparative examples did not obtain good results in any evaluation items.

INDUSTRIAL APPLICABILITY

The jelly preparation of the present invention can be gelatinized at normal temperature and can be dissolved at around intraoral body temperature because of inclusion of a gelatin. Physical properties, heat resistance, and the like in use of the jelly preparation can be significantly improved by addition of a trivalent metal ion.

In addition, since dissolution time of the jelly preparation can be easily adjusted by adjusting the addition amount of the trivalent metal ion, the jelly preparation of the present invention is suitable for oral desensitization therapy which requires control of sensitization time, and particularly for sublingual desensitization therapy. Furthermore, the adjustment of the moisture content enables easy adjustment of physical properties, heat resistance, and dissolution time.

Moreover, the jelly preparation can carry a higher amount (about 50%) of a drug than that of film preparations and orally disintegrating tablets. The jelly preparation can also contain macromolecular drugs such as proteins and peptides and aqueous solutions of drugs as well as low molecule drugs.

The jelly preparation of the present invention may naturally be swallowed as it is, or may be rapidly dissolved intraorally and then swallowed. In addition, the intraoral dissolution time is adjustable, and thus the preparation can be expected to be absorbed through the oral mucosa and sublingual mucosa. Since the preparation can be perfectly dissolved at body temperature and thus causes no feeling of residues, and since the surface area of the preparation in the case of having a sheet shape is larger than tablets and the like, whereby patients and caregivers can easily pick it up with their fingers, the jelly preparation of the present invention can greatly improve the QOL of patients and caregivers.

The invention claimed is:

1. A jelly preparation comprising:
   water,
   a gelatin,
   a drug, and
   a trivalent metal ion;
   wherein a gelatin content thereof is 10% to 50% by weight of the whole amount of the jelly preparation,
   wherein the trivalent metal ion is an aluminum ion,
   wherein the drug and aluminum ion are mixed in the gelatin, and
   wherein the preparation has a thickness within a range of 30 to 5,000 μm.

2. The jelly preparation according to claim 1,
   wherein the gelatin comprises a gelatin derived from porcine.

3. The jelly preparation according to claim 1,
   wherein a moisture content thereof is 5 to 90% by weight of the whole amount of the jelly preparation.

4. The jelly preparation according to claim 1,
   wherein the preparation has a plane area within a range of 0.5 to 6.0 cm$^2$.

5. A method of producing the jelly preparation according to claim 1, comprising the steps of:
   mixing water, a gelatin, a drug, and a trivalent metal ion to prepare a mixed solution, and
   forming a thin film from the mixed solution,
   wherein an amount of additive water is adjusted in the step of preparing a mixed solution, or a moisture content is adjusted by drying the thin film after the step of forming a thin film.

* * * * *